United States Patent [19]

Goldberg

[11] 4,226,713
[45] Oct. 7, 1980

[54] DIAGNOSTIC AGENTS

[76] Inventor: Jack M. Goldberg, 4612 W. Elm Ter., Skokie, Ill. 60076

[21] Appl. No.: 899,597

[22] Filed: Apr. 24, 1978

[51] Int. Cl.$^2$ .................... C09K 3/00; G01N 31/02; G01N 31/06; G01N 31/14; G01N 33/16
[52] U.S. Cl. .................... 23/230 B; 210/716; 424/3; 424/12; 252/408; 435/11; 260/112 R
[58] Field of Search .................... 424/3, 12; 23/230 B; 252/408; 210/42 R, 47, 52, 54

[56] References Cited

U.S. PATENT DOCUMENTS

| | | | |
|---|---|---|---|
| 3,955,925 | 5/1976 | Proksch et al. | 252/408 |
| 4,011,045 | 3/1977 | Bonderman | 252/408 |
| 4,039,285 | 8/1977 | Teipel | 252/408 |
| 4,045,176 | 8/1977 | Proksch et al. | 252/408 |
| 4,147,606 | 4/1979 | Golias | 424/12 |

OTHER PUBLICATIONS

Burstein, M. et al., J. Lipid Res., vol. 11, pp. 583–595, (1970).
Tietz, N. W., Fundamentals of Clinical Chemistry, W. B. Saunders Company, Philadelphia, Pa. pp. 539–540 (1976).

Primary Examiner—Teddy S. Gron
Attorney, Agent, or Firm—Mason, Kolehmainen, Rathburn & Wyss

[57] ABSTRACT

Diagnostic agents are described for determining high density lipoprotein cholesterol in body fluids such as serum or plasma. One is an enzymatic reagent for quantitative analysis for cholesterol composed of cholesterol oxidase, cholesterol esterase, peroxidase, 4-amino-antipyrine, a phenol or phenol derivative, a surfactant, such as sodium cholate and a polyglycol of molecular weight from about 190 to 1000, buffered to pH 5.5 to 7.8 in water. The other is a single, stable precipitating agent for lipoproteins in body fluids, comprising a bivalent metal salt of a monobasic acid, such as magnesium chloride and a water-soluble polyanion, such as sodium phosphotungstate in water at pH 5 to 8.

5 Claims, No Drawings

DIAGNOSTIC AGENTS

This invention relates to a diagnostic reagent for total and high density lipoprotein (HDL) cholesterol. More particularly the invention relates to a rapid, efficient and stable precipitating agent for preparing an HDL cholesterol fraction from a blood serum or plasma and a separate reagent for measuring such cholesterol.

BACKGROUND OF INVENTION

Cholesterol levels in blood are related to the risk factors associated with coronary heart disease. Efforts have been made to determine cholesterol level in blood of patients but none have provided a rapid and accurate procedure.

Considerable effort has been placed on trying to identify risk factors associated with coronary heart disease (CHD). The clinical laboratory has had its share of work in this effort with respect to lipoprotein analysis. Most laboratories offer cholesterol and triglyceride analysis, but recent studies are showing these tests to be about as obsolete as total lipid analysis. Electrophoresis of plasma lipoproteins gave some impetus to the presumptive phenotyping of patients, but this testing tended to focus on abnormalities of (low density lipoproteins) (LDL or $\beta$ lipoprotein) and very low density lipoproteins (VLDL or pre-$\beta$ lipoproteins) with very little interest shown in the high density lipoprotein (HDL or $\alpha$ lipoproteins). Clinical chemists are beginning to focus on some of the important epidemiological studies that have shown the probable value of HDL cholesterol estimations and show in pragmatic terms how this test can be incorporated into every routine clinical laboratory.

One of the earliest reports associating HDL with CHD was that of Barr et al, Am.J.Med. 11,480 (1951). In this study, the researchers made the observation that healthy men had higher HDL levels than did men with CHD. This finding was subsequently confirmed in many other studies. More recent publications involving large numbers of patient values have shown unequivocally the value of fractionating total cholesterol values into HDL and VLDL and LDL cholesterol.

HDL is a lipoprotein synthesized by the liver. One proposed mechanism of its action which fits with clinical data is that HDL is the transport mechanism which removes cholesterol from the peripheral tissues and carries it to the liver for catabolism. Thus, if the HDL levels are normal or high, then there is efficient removal of cholesterol which lowers the tissue pool and lessens the risk of deposition of cholesterol. Conversely, if the HDL levels are low, then there is inefficient removal of cholesterol and the subsequent risk of CHD is higher. Several observations lend support to this hypothesis.

1. In Tangier disease (deficiency of HDL) all patients have excessive deposition of cholesterol esters in the blood vessels.
2. Women have higher HDL levels than men and a lesser risk of developing CHD.
3. Blacks have higher HDL levels than whites with a lesser risk of developing CHD.
4. Children have higher HDL levels than adults, black children have higher levels than white children.
5. The prevalence of CHD in men aged 50–69 was double in the very low HDL groups compared to those above the population mean.

All of these studies were based on epidemiological data concerned with the prevalence of CHD. A few studies have now been conducted as prospective studies with respect to the incidence of the disease. In a report published in 1966 researchers suggested that the incidence of CHD was higher in young men with low HDL levels. A similar report was published in a study of middle aged men.

One of the most recent reports on the relationship between CHD and fasting plasma lipids was assessed by a case-controlled study in five populations with a total of 6,859 men and women of black, white and Japanese ancestry. In each major study, a statistically significant inverse relationship was found with CHD: it was found in most age-sex-race specific groups. These authors concluded that the "virtue of partitioning total cholesterol in assessing CHD risk is unequivocally demonstrated." HDL cholesterol has a negative correlation with CHD whereas LDL and VLDL cholesterol have a positive correlation with CHD. Hence, the "Total cholesterol (HDL & LDL & VLDL) must be a less sensitive indicator of risk than an appropriately weighted algebraic sum." Castelli et al. Circulation, 55 767 (1977).

Laboratory Evaluation of HDL Cholesterol

Two basic methodologies are available for HDL cholesterol measurement. The first widely used method was preparative ultracentrifugation. This is a very time consuming method with low productivity yield for a routine clinical laboratory. It also necessitates the availability of expensive equipment and highly trained personnel.

The second class of methods involves the precipitation of LDL and VLDL from serum or plasma by complexing them with a polyanion and divalent cation. Many procedures are based on precipitation of the LDL and VLDL with heparin and $Mn++$. However, most of these techniques suffer from the problems probably related to lot to lot variation in heparin. Recent literature contains many references of attempts to improve this assay.

In an attempt to try to improve the precipitation, polyanions other than heparin and cations other than $Mn++$ have been tried. One method which uses a phosphotungstate-$Mg++$ complex was recently re-evaluated and was shown to be a simple reliable method yielding results comparable to ultracentrifugation analysis. Burstein et al, J. Lipid Research, 11, 583 (1970).

Cholesterol Analysis

Measurement of serum or plasma cholesterol is technically difficult unless fairly specific analytical methods are used. It is highly doubtful that direct serum analysis by well known Liberman Buchard analysis for cholesterol will have the sensitivity or the accuracy necessary when dealing with low cholesterol levels found in the HDL fraction. As with most analytical methods, the closer to the limits of the instrumentation (such as spectrophotometers) one works, the greater the imprecision of the analysis. Furthermore, any interfering compounds will show a much greater percentage of error in the nonspecific methods. These technical difficulties can be overcome by use of extraction methods or the newer and technically simpler direct enzymatic procedures. Indeed, the enzymatic procedures lend themselves to the type of low level analysis since one can increase the sample size in an aqueous system.

Results of HDL cholesterol analysis should be presented to the clinicians in a usable report rather than a naked number. The report should describe the appearance of the serum, give total cholesterol, LDL cholesterol, HDL cholesterol, VLDL cholesterol and triglyceride values, each in mg/dl. In addition, the usual population ranges for these values should be given, as follows:

| Age | Total Cholesterol Male | Female |
|---|---|---|
| <20 | <180 mg/dl | |
| 20-30 | 140-260 | 140-240 |
| 30-40 | 140-280 | 140-240 |
| 40-50 | 140-280 | 150-280 |
| >50 | 140-280 | 180-330 |

| VLDL Cholesterol | |
|---|---|
| (calculated as Triglycerides/5) | |
| Male and Female | 0-40 mg/dl. |
| >40 associated with type II b, IV, or III Lipoproteinemias | |

| LDL Cholesterol | |
|---|---|
| Male | Female |
| 62-178 | 66-185 mg/dl |

Values greater than expected range are associated with a higher than average risk of coronary heart disease.

| HDL Cholesterol | |
|---|---|
| Male | Female |
| 29-61 | 38-75 |

Values below limits are associated with a higher than aveerage risk of CHD.
Values above 55 mg/dl. are associated with a lower than average risk of CHD.

Total and HDL Cholesterol values are measured analytes. VLDL cholesterol is calculated by dividing the serum or plasma triglycerides by five (valid only when triglycerides are less than 400 mg/dl and when no chylomicrons are present). The LDL cholesterol is then calculated as Total minus (HDL+VLDL) cholesterol.

SUMMARY OF THE INVENTION

Measurement of total cholesterol as an index of CHD risk has been demonstrated to be a less sensitive approach than fractionation of the total cholesterol into HDL and LDL components. The LDL cholesterol has a direct relationship to CHD whereas HDL has an inverse relationship to CHD. It is now possible, using simple techniques of polyanion fractionation and simple enzymatic cholesterol determinations, to provide clinicians with this newer tool for the assessment of risk of CHD. These tests can provide a large data base to identify the high risk population and perhaps aid in the search for factors that may elevate HDL levels thereby, hopefully favorably influence the health of the population.

High density lipoprotein (HDL) cholesterol has been shown to have an inverse correlation with ischemic heart disease and may be another good prognostic test to detect high risk subjects. Two basic methods are available to measure HDL. The first is ultracentrifugation analysis and the second is selective precipitation of the LDL and VLDL lipoproteins with divalent cations and polyanions.

The present invention is concerned with this second method of analysis based upon the selective precipitation of (1) the low density lipoprotein (LDL) and the very low density lipoprotein (VLDL) from (2) the high density lipoprotein to separate these two fractions for analysis, and particularly for analysis of the HDL. As set forth in an article by Burstein, et al., Journal of Lipid Research, Vol. II, 1970, pp. 583-595, low density lipoproteins and very low density lipoproteins (LDL+VLDL) have been selectively precipitated from serum or plasma without precipitation of the high density lipoproteins (HDL) remaining in the supernatant liquid first by the addition of (1) a polyanionic polysaccharide, or salt thereof such as heparin, dextran sulfate, mepesulfate, or sodium phosphotungstate followed by the addition of (2) a water soluble divalent cation, generally as a divalent metal salt of a monobasic acid, such as $MnCl_2$ or $MgCl_2$. It has been necessary to add each of these required precipitants separately, in prior art methods and using prior art reagents, since combining the two in the concentrations previously essential to achieve the required lipoprotein precipitation would create an unstable precipitating reagent in which a portion of the reagent would precipitate out, generally as a divalent salt, such as $MgCO_3$.

The measurement of serum or plasma cholesterol is technically difficult and must be precise as set forth above. The precipitating reagents must be added in exactly equal quantities to the serum or plasma being analyzed and to assure accurate measurement of serum cholesterol against the standard. The necessity for two separate additions of two separate precipitants, therefore, leaves room for error in both precipitant addition steps.

In accordance with an important feature of the present invention, it has been found that a divalent cation and a polyanion can be combined into a single, stable precipitating reagent without reagent precipitation prior to the addition of this single precipitating reagent to the cholesterol-containing body fluid. It has been found that by combining the bivalent cation, in a total precipitating reagent concentration of 0.25 to 0.75 molar, together with the water soluble polyanion in a concentration of 2 to 8% based on the total weight of the liquid precipitating reagent, the combined reagent will remain stable so that only one precipitation reagent addition is necessary—thereby significantly increasing the precision of each cholesterol analysis at the onset, in the initial separation of HDL from LDL and VLDL. The combined precipitating reagent including both the water soluble bivalent cation and the water soluble polyanion will remain stable and will not form a metal precipitate regardless of the particular bivalent cation and regardless of the particular polyanion so long as these two components are combined in these important concentration ranges. Examples of typical water soluble bivalent cation salts are $MgCl_2$, $MnCl_2$, $CaCl_2$ or any other water soluble bivalent metal salt of a monobasic acid. Commonly, the $MnCl_2$ and $MgCl_2$ and $CaCl_2$ salts are used in practice. Examples of typical water soluble polyanions are water soluble salts of phosphotungstic acid, such as sodium phosphotungstate; dextran sulfate; water soluble salts of heparin, such as the sodium salt; mepesulfate; and chondroitin sulfate. Commonly sodium phosphotungstate is used separately with $MgCl_2$ and dextran sulfate is used separately with $CaCl_2$ and heparin is used with $MnCl_2$.

After precipitation of LDL and VLDL cholesterol it is common procedure to analyze the HDL cholesterol by separately reacting the supernatant containing the HDL cholesterol from the serum or plasma sample with an enzymatic reagent to determine the relative color change. Cholesterol oxidase contained in the enzymatic reagent will react in the presence of the HDL cholesterol to produce hydrogen peroxide. Peroxidase, 4-aminoantipyrine and a phenol, also contained in the enzymatic reagent, then react with the hydrogen peroxide to produce quinonemine dye (red) which is analyzed on a spectrophotometer for comparison of (1) the dye produced in the sample obtained from serum or plasma, with (2) the dye produced in the cholesterol standard sample. Typical enzymatic reagents include cholesterol oxidase (microbial), cholesterol esterase (animal), peroxidase, 4-amino-antipyrine, phenol, a surfactant such as sodium cholate, a stabilizer, and a phosphate buffer in a water solution at a pH of 7.0. This enzymatic reagent is not stable for more than a few hours, and therefore is freeze dried for later water addition immediately prior to use. Accordingly, the enzymatic reagent must be freeze dried within a few hours after the composition is made or the entire batch is useless. Further, after the freeze dried reagent is solubilized (reconstituted) for later use in analysis, any excess enzymatic reagent which is not used within a few hours is wasted.

In accordance with an important feature of the present invention, it has been found that the addition of a water soluble polyglycol having an average molecular weight in the range of about 190–1000 will stabilize the enzymatic reagent for a period of seven days at a polyglycol concentration of 0.01–0.1%, based on the total weight of enzymatic reagent, when the reagent is kept refrigerated. An enzymatic reagent which is stable for seven days yields tremendous advantages both in manufacture of the enzymatic reagent and in use of the reagent to analyze cholesterol. There is no need to hurry the initial mixing of the enzymatic reagent components prior to freeze drying and there is no need to hurry freeze drying in the manufacture of the enzymatic reagent containing polyglycol in accordance with the present invention. After reconstitution of the freeze dried enzymatic reagent, generally with further addition of polyglycol to supplement the glycol rendered ineffective as a result of freeze drying, the reagent can be kept refrigerated for seven days so that the analyzing laboratory need not repeatedly and precisely reconstitute the enzymatic reagent for each sample, resulting in imprecision and waste of expensive excess reagent. Another important benefit derived from the addition of the polyglycol to the enzymatic reagent is that it substantially increases the activity of the enzymatic reagent.

Accordingly, an object of the present invention is to provide a new and improved method of manufacturing an enzymatic reagent useful in cholesterol analysis.

Another object of the present invention is to provide a new and improved enzymatic reagent useful in cholesterol analysis.

Another object of the present invention is to provide a new and improved enzymatic reagent useful in cholesterol analysis having dramatically improved stability or useful life.

Another object of the present invention is to provide a new and improved enzymatic reagent containing a water-soluble polyglycol surfactant capable of rendering the reagent stable for a substantial period of time.

Another object of the present invention is to provide a new and improved method of precipitating LDL and VLDL by the addition of a single, stable precipitating reagent thereto.

These and other objects and advantages of the present invention will become apparent from the following detailed description of the present invention.

DETAILED DESCRIPTION OF THE PRESENT INVENTION

A single, stable precipitant reagent is added to whole serum or plasma to precipitate LDL and VLDL, leaving the HDL in the supernatant liquid:

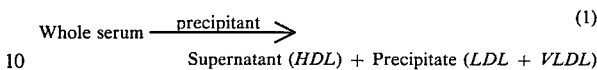

(1)

Supernatant (HDL) + Precipitate (LDL + VLDL)

The precipitant reagent (REAGENT 3) is a single, stable aqueous solution of a water-soluble bivalent metal salt of a monobasic acid together with a water-soluble polyanion, generally a polysaccharide or a polyphosphotungstate. It has been found that the bivalent salt and polyanion can be combined in a single, stable reagent so long as the concentration of the cation is in the range of 0.25–0.75 molar and the concentration of the polyanion is in the range of 2–8% by weight of the total precipitant reagent. The bivalent metal salt should be substantially colorless in salt, i.e. magnesium chloride, with the polyanion, i.e. phosphotungstate, in a single reagent, experimental error is minimized because only one addition of reagent is required and it is of larger volume which permits more accurate measurement in standard pipettes.

After addition of the precipitant reagent (REAGENT 3), the treated serum or plasma is centrifuged to segregate the precipitate (LDL and VLDL) from the supernatant liquid, containing the HDL fraction, and a precise quantity, i.e. 0.05 ml., of the supernatant is added to an enzymatic reagent capable of forming a chromophore. The enzymatic reagent contains cholesterol oxidase to produce $H_2O_2$, and contains 4-aminoantipyrine, peroxidase and a phenol or phenol derivative for reaction with the $H_2O_2$ to produce the chromophore. The reactions of the enzymatic reagent in the presence of HDL are as follows:

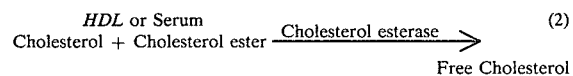

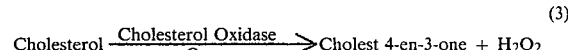

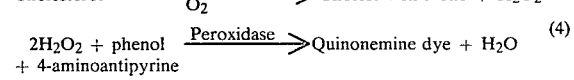

In addition to the essential components comprising the microbial cholesterol oxidase; animal cholesterol esterase; peroxidase; a bile salt, such as sodium cholate; 4-aminoantipyrine; an agent, such as phenol or a phenol derivative which forms a chromophore; and a water soluble polyglycol having a molecular weight of 190–1000, the enzymatic reagent should be at a pH in the range of 5.5 to 7.8 and therefore includes a buffer to maintain this pH during reaction. It may also be desirable to add an agent useful for maintaining the solubility of free cholesterol to prevent the reagent from becoming turbid as a result of precipitation of free cholesterol. One suitable cholesterol solubilizing agent is a water-soluble polyglycol having an average molecular weight of about 6000 or above. The bile salt maintains a homogeneous mixture of the enzymatic reagent when the reagent is reconstituted with water and aids in maintaining the cholesterol in solution. The bile salt can be any alkali metal cholate, glycocholate or desoxycholate.

The agent capable of forming a chromophore can be a phenol or phenol derivative such as phenol, 2,4-dichlorophenol, or o-dianisidine, cresol, caryacrol, thymol, and mixtures thereof. The polyglycol is contained in the enzymatic reagent in an amount of 0.01–0.1% based on the total weight of enzymatic reagent both before lyophilization and after the reagent is reconstituted to assure stability.

It has been found that a portion of the enzymatic reagent can be separated and maintained as a stable liquid which can be added to a dry, powder composition containing the remainder of the enzymatic reagent when reconstituted for use in analysis. It has been found that the phenol or phenol derivative, bile salt, and polyglycol can be separated and maintained stable as a separate liquid reagent (REAGENT 2) thereby reducing manufacturing costs in initially preparing a dry powder composition which does not require lyophilization, as an alternative to expensive lyophilization. In this manner, an enzymatic reagent is prepared in two components: DRY FILLED REAGENT 1: microbial derived cholesterol oxidase, animal derived cholesterol esterase, peroxidase, and 4-aminoantipyrine and a buffer suitable to maintain a pH of 5.5 to 7.8, and LIQUID REAGENT 2: phenol or phenol derivative capable of forming a chromophore (yields a measurable color), bile salt such as sodium cholate, and a water soluble polyglycol having an average molecular weight in the range of about 190–1000. Both DRY FILLED REAGENT 1 and LIQUID REAGENT 2 are stable for substantial periods of time of 6 months or more. To reconstitute the enzymatic reagent for use in analysis, REAGENT 1 is dissolved in REAGENT 2 to provide an enzymatic reagent stable for seven days, when kept refrigerated (0° to 10° C.).

Alternatively, all components of the enzymatic reagent can be lyophilized and later reconstituted by adding the lyophilized reagent to an aqueous solution of a water soluble polyglycol having an average molecular weight in the range of 190–1000.

DETAILED DESCRIPTION OF THE PREFERRED EMBODIMENT

In accordance with a preferred embodiment of the present invention, the above-described agents are provided in kit form as four separate reagents. Reagents 1 and 2 are combined to form the working cholesterol reagent (ENZYMATIC REAGENT) to which the supernatant liquid containing HDL is added. Reagent 3 is the PRECIPITANT for the initial precipi is provided as the CHOLESTEROL STANDARD. Each kit contains the following reagents for in vitro diagnostic use:

4 vials DRY FILLED REAGENT 1 containing 100 U/l cholesterol oxidase (microbial) (50 to 250 U/l.)* 50 U/l cholesterol esterase (animal) (20 to 200 U/l.)* $40 \times 10^3$ U/l peroxidase (horseradish) ($10 \times 10^3$ to $100 \times 10^3$ U/l.)* 0.06% (w/v) 4-aminoantipyrine (0.015% to 0.1% (w/v) solution)* phosphate buffer to pH of 7.0, and a stabilizer (polyethylene glycol having an average molecular weight approximately 6000 or higher), (1 to 2 gm./l)*.

4 vials LIQUID REAGENT 2 each containing 25 ml of an aqueous solution containing: 0.1% (w/v) phenol (0.02% to 0.2% (w/v) solution)* a surfactant, such as sodium cholate (0.01% to 1.0% (w/v))* and a water-soluble polyglycol having an average molecular weight in the range of 190 to 1000, (0.01% to 0.1% (w.v))*.

1 vial REAGENT 3 containing 10 ml precipitating solution of 0.5 molar water-soluble bivalent metal salt of a monobasic acid, such as magnesium chloride (0.25 to 0.75 molar) in a water-soluble polyanion, such as an alkali metal phosphotungstate solution (2% to 8%).

1 vial containing 250 mg/dl cholesterol standard in aqueous base.

*Data in parentheses indicate the concentration range to achieve the full advantage of the present invention.

Reconstitution of Reagents: To prepare working cholesterol reagent (ENZYMATIC REAGENT), add the contents of one vial of REAGENT 1 to one vial of REAGENT 2. Allow approximately 10 minutes for complete solution, then swirl the vial to mix completely. The resulting ENZYMATIC REAGENT is STABLE for 7 days when refrigerated (2° to 10° C.). The working cholesterol reagent (REAGENT 1 plus REAGENT 2) should be almost colorless. A faint pink color is allowable if the absorbance of the solution at 510 nm measured against water is less than 0.10. REAGENT 3 and the CHOLESTEROL STANDARD are used without dilution.

Suitable polyglycols for use in initially preparing the ENZYMATIC REAGENT prior to lyophilization, and for reconstitution of the ENZYMATIC REAGENT include polyethylene glycols 200, 300, 400, 500, 600, 800 and 1000, which are glycols of the general formula

where n is number from about 4 to about 20. The numbers 200, 300, . . . represent the approximate average molecular weight of the polyethylene glycols. Other suitable polyglycols include aromatic ethers of polyethylene glycols such as Triton X-100 of Rohm and Haas Company which is a water-soluble isooctylphenoxypolyethoxyethanol containing nine or ten ethoxy groups having the general formula

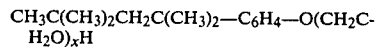

wherein the average value of x is ten. A polyglycol known as Adekatol or Leonol (a polyethoxy glycol having 16 carbon atom units) sold by Leon Laboratories is also suitable and has been found to be particularly commercially acceptable. All of these glycols are viscous syrups which are soluble in water at the concentrations (0.25 to 0.75 gram per liter) required for use in the present invention to provide exceptional ENZYMATIC REAGENT stability and activity.

Polyethylene glycol 200 has an average molecular weight from 190 to 210. Polyethylene glycol 300 has an average molecular weight from 285 to 315. Polyethylene glycol 400 has an average molecular weight from 380 to 420. All of these glycols are clear viscous liquids which dissolve readily in water. Other polyglycols containing 8 to 20 carbon atoms are suitable.

The pH of the precipitant solution (REAGENT 3) is is preferably maintained at about 7.0 although pH's of 5.5 to 7.8 are suitable.

The stabilizer in REAGENT 1 may not be essential since the polyglycol of REAGENT 2 generally is sufficient for stabilization and cholesterol solubilization. When a stabilizer is used in REAGENT 1, polyethylene glycol 6000 is preferred and is present at a concentration of about 1 to 1.5 g/l. Other high molecular weight polyethylene and polypropylene glycols can be substituted for PEG 6000 so long as they are water-soluble at concentrations of 1 g/l. The purpose of the stabilizer is to aid in solubilizing the cholesterol and is unnecessary in reconstitution because of the polyglycol used in initial manufacture of lyophilized REAGENT 1 and in reconstitution with REAGENT 2.

The surfactant in REAGENT 2 is a combination of a bile salt, such as an alkali metal cholate, at a weight percentage of from 0.01% to 1.0% and a polyglycol having an average molecular weight from approximately 190 to 1000 at a weight percentage of from 0.01% to 0.1%. The surfactant stabilizes the cholesterol esterase and activates the cholesterol esterase and the cholesterol oxidase.

When the combined working reagent (REAGENTS 1 plus 2), or a concentrate thereof, are mixed and lyophilized (freeze-dried) at 30 microns pressure and a final temperature of 26° C., the dry product can be reconstituted by dissolution in an aqueous solution containing 0.01 to 0.1% of a water-soluble polyglycol having an average molecular weight of 190-1000. This procedure stabilizes the enzymes throughout the resulting ENZYMATIC REAGENT.

Interfering Substances: A list of potential interfering compounds has been published in Young, Clin. Chem., 21, 1D-432D (1975). To date, no known compound present in physiological concentration in serum is known to interfere in the cholesterol analysis. Various lipoproteinemias and other dysproteinemias may interfere with the full precipitation of LDL and VLDL.

Specimen: The preferred specimen is serum following a 14-hour fast. The patient should have been on a full ethnic diet for several days before blood sampling. Serum should be stored at room temperature where it is stable for at least 5 days. Refrigeration or freezing of samples may alter the structure of the lipoproteins yielding lower results.

Assay Procedure (a) Preparation of HDL Fraction
1. Pipet 1 ml serum into labelled conical centrifuge tube.
2. Add 0.1 ml REAGENT 3. Mix well.
3. Centrifuge tubes at 1000×g (full speed for most bench centrifuges) for 15 minutes.
4. Carefully remove clear supernatant fraction and transfer to a labelled tube marked HDL fraction. (Note: if the supernatant is turbid as may happen with lipemic samples, dilute serum 1/1 with saline and repeat precipitation. Multiply the final result by 2.)

(b) Assay of Total and HDL Cholesterol
1. Label assay tubes, one for reagent blank, one for standard and one for each sample to be analyzed.
2. Pipet 2 ml of working cholesterol reagent into each tube and place in 37° C. water bath for 2 minutes to equilibrate to temperature.
3. Add the following samples to appropriate tubes: standard and whole serum —20 microliters; HDL fraction —50 microliters.
4. Mix well and incubate tubes for 15 minutes.
5. Remove tubes from water bath and read before 30 minutes.
6. Blank photometer to zero with reagent blank at 510 nm.
7. Read and record the absorbance of each tube at 510 nm.
8. Samples greater than 500 mg/dl should be diluted 1:1 with saline and reassayed. Multiply result by 2.

(c) Calculations

1. $$\text{Total cholesterol.} = \frac{\text{absorbance sample}}{\text{absorbance standard}} \times \frac{\text{concentration standard}}{1}$$

Example $\frac{0.484}{0.390} \times \frac{250}{1} = 310$ mg/dl

2. $$\text{HDL Cholesterol} = \frac{\text{absorb sample}}{\text{absorb standard}} \times \frac{\text{concentration standard}}{1} \times \frac{0.447}{1}$$

The factor 0.447 is derived from the dilution of the sample with REAGENT 3 and using 50 μl sample v. 20 μl standard.

Example $\frac{0.170}{0.390} \times \frac{250 \times 0.447}{1} = 48$ mg/dl HDL Chol.

Expected Values: One study performed using this kit resulted in a range of 30–75 mg/dl for HDL cholesterol and 130–280 mg/dl for total cholesterol.

Performance Characteristics: Precipitation of LDL and VLDL lipoproteins assessed by electrophoresis was 100%.

Linearity of the cholesterol assay was to 500 mg/dl.

The absorbancy of the 250 mg/dl cholesterol standard was 0.390±0.03. This will vary with the accuracy of the micropipet used.

Precision studies of a lyophilized control serum analyzed daily for 20 days was: mean 230 mg/dl and C. V. 2.2%.

EXAMPLE 1

Reagent 1 is a dry powder containing 100 units per liter of cholesterol oxidase, 50 units per liter of cholesterol esterase, 40,000 units per liter of peroxidase, 0.06% (w/v) 4-aminoantipyrine and 1.15 grams per liter of polyethylene glycol 6000 as stabilizer. Phosphate buffer (14.2 g. $Na_2HPO_4$ and 7.5 g. $KH_2PO_4$ per liter) is included to adjust the pH of the reagent to a value between 6 and 8, preferably 7.

Reagent 2 is produced by dissolving 2 grams of sodium cholate in 900 ml of distilled water. Then 0.5 ml of polyethylene glycol or molecular weight from 190 to 1000 is dissolved in the solution, followed by 1.1 ml of a 90% aqueous solution of phenol.

Reagent 3 is made by dissolving 40 grams of phosphotungstic acid in 700 ml of distilled water. To the resulting solution is added 60 ml of a 10% (w/v) solution of NaOH and 100 grams of $MgCl_2.6H_2O$. The solution is then diluted to one liter volume. Its pH is 6.8±0.2.

Reagents 1 and 2 are admixed to form the cholesterol reagent, which is stable for at least a week when refrigerated (2° to 10° C.).

What is claimed and desired to be secured by Letters Patent of the United States is:

1. A method of precipitating LDL and VLDL lipoproteins from a body fluid comprising:
adding to the body fluid a single precipitating agent comprising a stable aqueous solution of magnesium chloride which salt is colorless in 0.5 molar solution and a water-soluble phosphotungstate in concentrations relative to the body fluid of 0.025 to 0.075 millimoles of magnesium chloride per millimeter of body fluid and 0.002 to 0.008 grams of phosphotungstate polyanion per milliliter of body fluid; and clarifying the solution of the precipitating agent and the body fluid to yield a supernatant solution containing HDL as substantially the only form of cholesterol in solution.

2. A method of precipitating LDL and VLDL lipoproteins from a body fluid comprising:

adding a single precipitating agent, made by the addition of magnesium chloride to neutralized phosphotungstic acid, to a body fluid wherein said magnesium chloride is colorless in 0.05 molar solution, and wherein said neutralized phosphotungstic acid is a water-soluble phosphotungstate to provide a concentration of said magnesium chloride of 0.025 to 0.075 millimoles per milliliter of body fluid and a concentration of phosphotungstate polyanion of 0.002 to 0.008 grams per milliliter of body fluid; and clarifying the solution of the precipitating agent and body fluid to yield a supernatant solution containing HDL as substantially the only form of cholesterol to quantitatively determine the HDL.

3. A method as defined in claim 2 wherein said precipitating agent contains said magnesium chloride in a concentration of 0.25 to 0.75 molar and wherein said precipitating agent contains said phosphotungstate anion in a concentration of 2% to 8% by total weight of said precipitating agent.

4. A method as defined in claim 2 wherein said agent has a pH of $6.8 \pm 0.2$.

5. A method as defined in claim 2 wherein said phosphotungstic acid is neutralized to a pH of $6.8 \pm 0.2$.

* * * * *